(12) United States Patent
Kantola et al.

(10) Patent No.: US 11,185,617 B2
(45) Date of Patent: Nov. 30, 2021

(54) DRAINAGE SYSTEM WITH RETENTION RING

(71) Applicant: Becton, Dickinson and Company, Franklin Lakes, NJ (US)

(72) Inventors: James C. Kantola, Waukegan, IL (US); Shayna Massi, Palatine, IL (US); John A. Krueger, Muskego, WI (US); Daniel A. Gorsky, Lebanon, OH (US); Robert Gerald States, III, Morrow, OH (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 418 days.

(21) Appl. No.: 15/664,968

(22) Filed: Jul. 31, 2017

(65) Prior Publication Data

US 2019/0030219 A1    Jan. 31, 2019

(51) Int. Cl.
*A61M 1/00* (2006.01)
*A61J 1/14* (2006.01)
*A61J 1/20* (2006.01)

(52) U.S. Cl.
CPC .......... *A61M 1/0001* (2013.01); *A61J 1/1406* (2013.01); *A61J 1/1412* (2013.01); *A61J 1/201* (2015.05); *A61M 1/0003* (2013.01); *A61M 1/86* (2021.05)

(58) Field of Classification Search
None
See application file for complete search history.

(56) References Cited

U.S. PATENT DOCUMENTS

| | | | | | |
|---|---|---|---|---|---|
| 2,894,425 | A | * | 7/1959 | Rapata | F16B 21/186 411/360 |
| 2,925,187 | A | * | 2/1960 | Bramming | A47J 41/0011 215/12.1 |
| 4,431,111 | A | * | 2/1984 | Prohaska | B65D 41/44 215/256 |
| 4,447,235 | A | | 5/1984 | Clarke | |
| 4,522,308 | A | * | 6/1985 | Sullivan | B65D 41/485 215/253 |

(Continued)

OTHER PUBLICATIONS

Pinto, et al. "Large-Volume Paracentesis in Nonedematous Patients With Tense-Ascites: its Effect on Intravascular Volume," Hepatology, vol. 8, No. 2, pp. 207-210, 1988.

(Continued)

*Primary Examiner* — Tatyana Zalukaeva
*Assistant Examiner* — Jessica R Arble
(74) *Attorney, Agent, or Firm* — Dinsmore & Shohl LLP

(57) ABSTRACT

In one general aspect, the present disclosure provides a drainage system. The drainage system may include a container having an interior and a mouth, the mouth having an outer surface and an opening. A frangible seal may cover the opening. A cap may be secured to the mouth, and the cap may be in fluid communication with a drainage line. The cap may have an inner surface for engaging with the outer surface of the mouth. The drainage system may further include a retention ring with a collar having an inner surface configured to engage an outer surface of the cap, where the retention ring includes a bead for at least partially concentrating a restriction force provided by the retention ring on an adjacent area of the outer surface of the cap.

20 Claims, 8 Drawing Sheets

(56) References Cited

U.S. PATENT DOCUMENTS

| | | | | |
|---|---|---|---|---|
| 4,582,207 A * | 4/1986 | Howard | ............... | B65D 51/002 215/247 |
| 4,773,553 A * | 9/1988 | Van Brocklin | ..... | B05B 11/3049 215/272 |
| 4,784,156 A | 11/1988 | Garg | | |
| 4,832,044 A | 5/1989 | Garg | | |
| 4,840,184 A | 6/1989 | Garg | | |
| 4,844,087 A | 7/1989 | Garg | | |
| 5,279,576 A * | 1/1994 | Loo | ....................... | A61J 1/2096 222/1 |
| 5,334,159 A | 8/1994 | Turkel | | |
| 5,484,101 A | 1/1996 | Rodriguez et al. | | |
| 5,725,506 A | 3/1998 | Freeman et al. | | |
| 6,341,706 B1 * | 1/2002 | Neuner | ................ | B65D 45/322 215/40 |
| 6,957,745 B2 * | 10/2005 | Thibault | ............... | A61J 1/1406 141/330 |
| 7,048,724 B2 * | 5/2006 | Grossman | ........... | A61M 1/0003 604/319 |
| 2004/0116902 A1 * | 6/2004 | Grossman | ........... | A61M 1/0027 604/540 |
| 2008/0073314 A1 * | 3/2008 | Condon | ................. | B65D 39/00 215/364 |
| 2009/0308025 A1 * | 12/2009 | Martin | .................. | B67B 3/2066 53/317 |
| 2011/0126675 A1 * | 6/2011 | Ferraro | ................ | B65D 51/228 81/3.07 |
| 2012/0037654 A1 * | 2/2012 | McNamara | ........ | B65D 43/0212 220/784 |
| 2015/0013811 A1 * | 1/2015 | Carrel | ................... | A61J 7/0472 137/798 |
| 2016/0023812 A1 * | 1/2016 | Kikel | ..................... | B65D 53/02 235/492 |
| 2016/0137474 A1 * | 5/2016 | Marantis | ................ | A61J 1/14 141/331 |
| 2017/0000933 A1 * | 1/2017 | Lopez | ................. | A61M 1/0027 |
| 2017/0297781 A1 * | 10/2017 | Kawamura | ............ | B65D 51/18 |
| 2020/0216218 A1 * | 7/2020 | Sanbar | ................. | B65D 47/249 |

OTHER PUBLICATIONS

Izbicki et al., "Pleural Effusion in Cancer Patients", Cancer, Oct. 1975 p. 1511.

* cited by examiner

DRAINAGE SYSTEM WITH RETENTION RING

TECHNICAL FIELD

The present invention relates to the field of medical devices and, in particular, to a device useful for withdrawing and containing fluids from a patient body.

BACKGROUND

Body fluids may need to be withdrawn from a patient in the course of medical treatment. Two common medical procedures requiring fluid removal are thoracentesis and paracentesis.

In paracentesis, peritoneal fluid is aspirated from the abdomen. Typical patients have tense ascites resulting from liver disease and portal hypertension, which may cause discomfort, respiratory distress, and the formation and rupture of umbilical hernias. Paracentesis has been observed to provide quick and effective relief with few adverse side effects. Other treatment options, such as the use of diuretics, are available, but may not provide as effective relief as paracentesis. Additionally, many patients with ascites have renal impairment and cannot use the high doses of diuretics necessary to effectively treat the ascites. See "Large-Volume Paracentesis in Nonedematous Patients with Tense-Ascites: Its Effect on Intravascular Volume," Pinto et al., *Hepatology*, Vol. 8, No. 2, pp. 207-210, 1988. Relatively large volumes of fluid, such as five liters, may be withdrawn from a patient during one paracentesis procedure.

Many existing devices are capable of performing paracentesis. At its simplest, a paracentesis device need only include a hollow needle with one end inserted into the patient and the other end attached to a negative pressure device, such as a syringe or vacuum bottle. However, more specialized devices have been developed to allow safer, more comfortable, and more sanitary paracentesis. These devices may allow for body fluid to be dispensed into at least two containers, so that one container may be filled with fluid for diagnostic purposes and the other container may be filled with waste fluid. Another development has been the use of Kuss or Verres type needle assemblies, where a blunt drainage needle is attached to a retractile sharp introducer needle. This reduces the likelihood of the sharp needle damaging internal tissue during paracentesis. A further development is to drain body fluid through a blunt-tipped catheter introduced by a sharp introducing needle, which allows the sharp needle to be removed from the patient after a relatively quick introduction process and avoids the prolonged presence of a sharp needle in the body of the patient.

Problems may arise when drainage is diverted from one container to another if the drainage system is not airtight. Air could contaminate a sample or enter the body of the patient and cause injury. Known devices that are meant to be airtight have tubes and multiple containers attached to the devices which make the devices cumbersome and somewhat difficult to insert into the patient. Also, known devices require manipulation of a manual valve, such as a stopcock to work effectively. If the stopcock is not set at the proper setting, the device may admit air into the patient or otherwise malfunction. Problems also may arise in devices which allow a needle assembly to be withdrawn. Air must be prevented from entering the patient when the fluid is withdrawn. Also, body fluid must be prevented from leaking out of the device through the space formerly occupied by the needle assembly.

Thoracentesis is a procedure similar to paracentesis, except that effusion fluid is withdrawn from the pleural region instead of the abdomen. Normally, the pleural space contains approximately 5 to 20 ml of fluid. The fluid is the result of the hydrostatic-oncotic pressure of the capillaries of the parietal pleura. The turnover of the fluid in the pleural space is normally quite rapid, so that approximately 0.5 to 5 liters (e.g., 1 to 2 liters) of fluid move through the pleural space each day. A disruption in the balance between the movement of fluid into the pleural space and the movement of fluid out of the pleural space may produce excessive fluid accumulation in the pleural space. Pleural effusion is particularly common in patients with disseminated breast cancer, lung cancer or lymphatic cancer and patients with congestive heart failure, but also occurs in patients with many other forms of malignancy.

Pleural effusion may cause dyspnea, coughing, and chest pain, which diminish a patient's quality of life. Although pleural effusion typically occurs toward the end of terminal malignancies, such as breast cancer, it occurs earlier in other diseases. Therefore, relieving the clinical manifestations of pleural effusion is for real and extended advantage to the patient. For example, non-breast cancer patients with pleural effusion have been known to survive for years. See "Pleural Effusion in Cancer Patients," Izbicki et al., *Cancer*, October 1975, p. 1511.

There are several treatments for pleural effusion. If the patient is asymptomatic and the effusion is known to be malignant or paramalignant, no treatment may be required. Pleurectomy and pleural abrasion are generally effective in obliterating the pleural space, thus controlling the malignant pleural effusion. However, pleurectomy is a major surgical procedure associated with substantial morbidity and some mortality. Chemotherapy is generally disappointing; however, it may produce good responses for patients with lymphoma, breast cancer, or small-cell carcinoma. Another approach is to surgically implant a chest tube. However, such a tube is painful to the patient, both when it is inserted and during the time that it remains in the pleural space. Improvements on the traditional chest tube are described in U.S. Pat. No. 5,484,401.

Despite other treatment options, thoracentesis remains the most common approach to removing pleural fluid. However, thoracentesis poses the danger of causing pneumothorax, a collapsed lung. Pneumothorax can be caused directly by puncturing a lung with a needle assembly or catheter tip or indirectly by allowing air to enter the pleural space. Normally, the pleural space is at negative pressure relative to the atmosphere, which helps keep the lungs expanded. If the atmosphere is allowed to communicate with the pleural space, the pleural space may no longer be at negative pressure and pneumothorax may result.

Thoracentesis devices have been developed to reduce the risk of pneumothorax and other similar problems that may result from the procedure. In general, these devices incorporate similar protections as do paracentesis devices. For example, U.S. Pat. No. 4,447,235 by Clarke discloses a thoracentesis device with a catheter introduced by a removable needle assembly, with a valve that closes upon removal of the needle assembly. The purpose of the valve is to prevent air from entering the body of the patient. U.S. Pat. Nos. 4,784,156, 4,832,044, 4,840,184, and 4,844,087 by Garg disclose similar devices with a manual valve that may be closed after withdrawal of the needle assembly. However, none of the previous devices allow for a truly fail-safe operation, as various valves must be properly set by the operator when changing from one drain port to another or when withdrawing the introducing needle assembly from the patient. Also, care must be taken to avoid accidental withdrawal of the introducing needle assembly, as in the disclosed devices where the needle assembly is not firmly attached to the remainder of the device. Further, the disclosed valves that allow for catheter drainage after removal of an introducing needle assembly rely on a single contact point. Due to the possibly dire consequences of a valve failure, such valves may not produce acceptably safe thoracentesis.

A Verres-type needle assembly that may be used for thoracentesis is disclosed in U.S. Pat. No. 5,334,159 by Turkel. While this reduces the risk of pneumothorax due to lung puncture, the Turkel device does not improve the safety of thoracentesis when the introducing needle assembly is withdrawn or solve the problems associated with multiple drainage ports. Thus there is a need for a safer and more reliable device that may be used for paracentesis and thoracentesis. Another device is described in U.S. Pat. No. 5,725,506 by Freeman, et al., which is incorporated by reference herein in its entirety.

Other difficulties with existing systems relate to manufacturing, storing and using the vacuum element. Syringes are sometimes used to generate the vacuum, but syringes are somewhat complicated to manufacture and use. An alternative vacuum source is a vacuum bottle. In that approach, a vacuum is created in an air-tight bottle at the manufacturing stage, and then the bottle is sealed. The bottle is then tapped at the time of use so that the vacuum can be applied to a drainage line to remove the undesired body fluids.

This is quite elegant in concept but somewhat difficult to implement perfectly in every individual unit. There is always some risk that the vacuum will be lost in transit before use, either by leaks, fractures or just air permeating through a plastic wall. Moreover, the loss of vacuum is not necessarily apparent to the user; a bottle with a perfect vacuum inside looks no different than a bottle of air, but the drainage efficacy of the unit may be diminished upon loss of vacuum before use or during use where the vacuum is wasted on pulling in air rather than exerting drainage effectively from the patient. Another problem is in tapping the bottle. This requires a system that pierces a vacuum seal but does not allow air to enter the bottle, except through the draw line. One such system is described in commonly owned U.S. Pat. No. 7,048,724 by Grossman et al, which is incorporated by reference herein in its entirety.

In known systems utilizing a vacuum bottle, a cap may be provided that acts as an interface between the bottle and a drainage line. In practice, it is typical for the junction of the cap and the bottle to be assembled with the use of an adhesive, such as a silicone adhesive gel. The silicone gel may act both to secure the cap to the bottle and to create a fluid seal at the junction.

Systems using a silicone adhesive have achieved positive results. However, silicone gel adhesive typically is expensive and manufacturing expenses associated with applying a silicone gel remain high. Further, it can be difficult to apply a precise amount of adhesive during the assembly process to achieve consistent securing and sealing that will patently maintain desired vacuum throughout the device live and usage. Silicone adhesives also typically can only dry and set one time, shortly after application, and therefore the system is generally shipped fully assembled, and it may be difficult to interchange the vacuum bottles at the medical facility. Further, the use of an suitable amount of adhesive to form an adequate seal may secure the cap the bottle to a degree such that is difficult to remove by a user, thus making it difficult for user the to remove the cap prior to disposing medical waste collected within the bottle.

In light of this background, it would be advantageous to provide an improved system utilizing a container, such as a vacuum bottle, connected to a drainage line that achieves sufficient securing and sealing between the container and cap without the need for the use of an adhesive, that can be removed by a user without undue force for purposes of waste disposal.

BRIEF SUMMARY

In one general aspect, the present disclosure provides a drainage system. The drainage system may include a container having an interior and a mouth, the mouth having an outer surface and an opening. A frangible seal may cover the opening. A cap may be secured to the mouth, and the cap may be in fluid communication with a drainage line. The cap may have an inner surface for engaging with the outer surface of the mouth. The drainage system may further include a retention ring with a collar having an inner surface configured to engage an outer surface of the cap, where the retention ring includes a bead for at least partially concentrating a restriction force provided by the retention ring on an adjacent area of the outer surface of the cap.

In some embodiments, the outer surface of the mouth includes a protrusion, where the bead of the retention ring is located distally of the protrusion of the mouth. The retention ring may include a tab extending from the collar, the tab having a surface for receiving a removal force. The collar of the retention ring may include a collar portion having a relatively low bending moment of inertia with respect to adjacent areas of the collar such that the collar portion deforms in response to the removal force being received by the tab. The surface of the tab of the retention ring may face distally, and the tab of the retention ring may include a rib on its proximal side extending to a lip of the collar. The retention ring may include a prong with a point for increasing the size of an opening of the frangible seal.

In some embodiments, the drainage system may include a spike with a flange, the spike being configured to pierce the frangible seal in response to an initiation force being applied to the flange in a distal direction The drainage system may further include a safety clip engaged with the cap and located at least partially between the flange of the spike and the retention ring. The safety clip may include a groove for receiving at least a portion of the collar of the retention ring.

In another general aspect, the present disclosure provides a retention ring for a drainage system. The retention ring may include a collar having an inner surface forming a generally circular opening and a bead extending from the inner surface of the collar. The bead may be configured for at least partially concentrating a restriction force on an adjacent area of an outer surface of a cap.

In some embodiments, the retention ring may include a tab extending from the collar, where the tab has a surface for receiving a removal force. The collar of the retention ring may include a collar portion having a relatively low bending moment of inertia with respect to adjacent areas of the collar such that the collar portion deforms in response to the removal force being received by the tab. The surface of the tab of the retention ring may face distally, and the tab of the retention ring may include a rib on its proximal side extending to a lip of the collar. The rib may include a gusset. The retention ring may additionally or alternatively include a prong with a point for increasing the size of an opening of a frangible seal. A 3-D printing process may be used to form the retention ring, and the retention ring may include at least one of a polypropylene material and a nylon material.

In another general aspect, the present disclosure provides a method. The method may include piercing a frangible seal with a spike where the frangible seal covers an opening of a mouth of a container and exposing a drainage line to a vacuum initially contained in an interior of the container. A cap may provide fluid communication between the interior of the container and the drainage line, where the cap is engaged with an outer surface of the mouth, where a seal is provided between the outer surface of the mouth and the cap by a compression force, where the compression force is provided by a collar of a retention ring, the collar including an inner surface positioned in engagement with an outer surface of the cap, and where the inner surface of the collar includes a bead for at least partially concentrating the compression force on an area of the cap adjacent to the bead.

In some embodiments, the outer surface of the mouth may include a protrusion, where the bead of the retention ring is located distally of the protrusion of the mouth. The method may further include removing the retention ring from engagement with the cap by applying a removal force to a tab of the retention ring, where the tab of the retention ring is coupled to the collar of the retention ring, and where a collar portion of the collar bends in response to the application of the removal force. The method may additionally or alternatively include the step of increasing the size of an opening of the pierced frangible seal by manipulating a prong of the retention ring through the opening.

DETAILED DESCRIPTION

Figure 1:
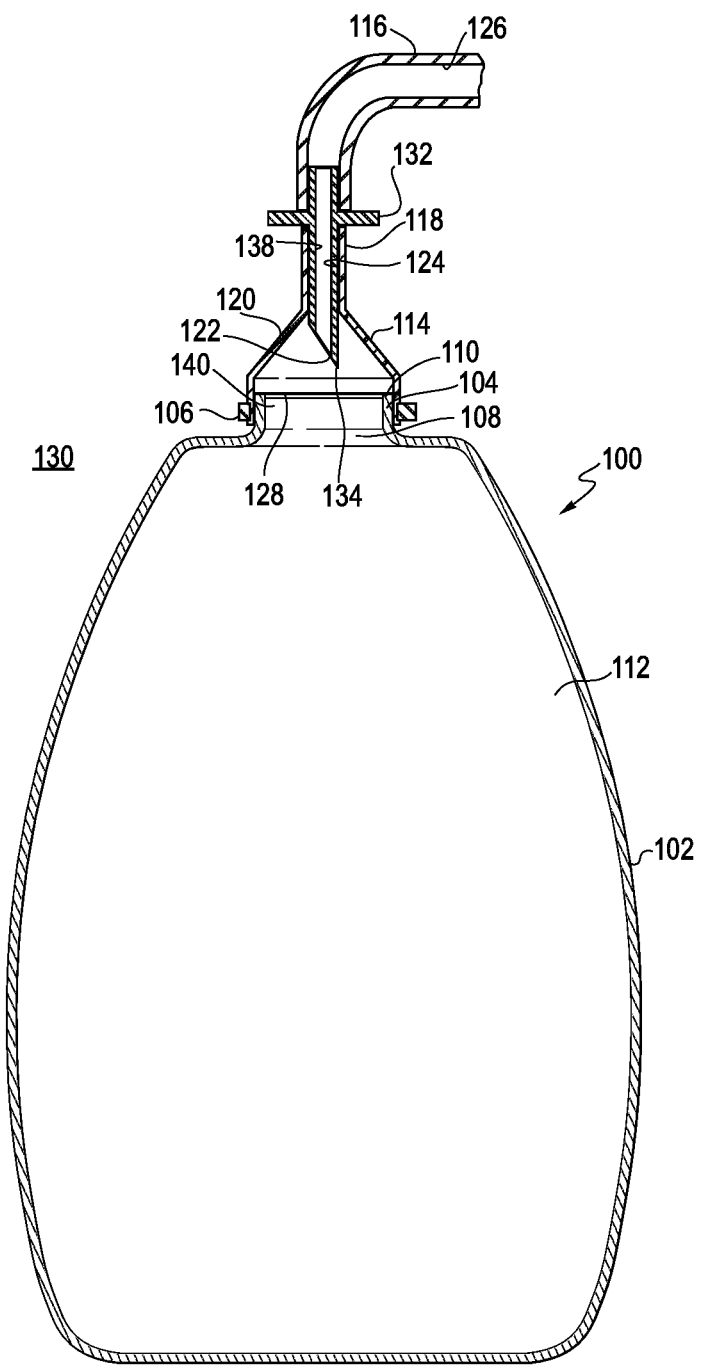
FIG. 1 is an illustration showing a front cut-out schematic of one embodiment of a drainage system with a retention ring in accordance with the present disclosure.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

FIG. 1 is an illustration showing a front cut-out schematic of one embodiment of a drainage system 100. Referring to FIG. 1, the drainage system 100 may include a container 102, which may be a bottle or a vacuum bottle (or other suitable container). The container 102 may have a mouth 104 with an outer surface 106 and an opening 108 at its proximal end 110. The opening 108 may lead to an interior 112 of the container 102. During a drainage procedure, a cap 114 may cover the opening 108 of the mouth 104 and may lead to a drainage line 116. The cap 114 may have a sleeve 118 at its upper (distal) end and a widened body 120 at its lower (proximal) end. The sleeve 118 of the cap 114 may receive a spike 122 in a manner such that a substantially air-tight seal is formed between the exterior surface of spike 122 and a lumen 124 of sleeve 118.

The lower end of spike 122 may terminate at a point 134. The upper end of spike 122 may receive the drainage line 116. Like the connection between spike 122 and the sleeve 118 of the elastomeric cap 114, the connection between spike 122 and drainage line 116 is preferably substantially air-tight. The spike 122 may also include a circumferential flange 132 to assist in manipulating the spike 122 in relation to container 102 in the manner described below. A lumen 138 may extend through spike 122 such that a lumen 126 of the drainage line 116 can communicate with the container 102 during a drainage procedure.

A frangible seal 128 may cover the opening 108 of the mouth 104 prior to initiation of the drainage procedure. Prior to being pierced, the frangible seal 128 may seal the interior 112 of the container 102 from the external environment 130. More particularly, the frangible seal 128 may be constructed of foil, mylar, or other substantially air-tight material to prevent air or other fluid from leaking into the interior 112 of the container 102 to spoil a pressure differential (e.g., a relative vacuum) between the interior 112 and the external environment. In some embodiments, the pressure differential may be at least 10 psi (e.g., 13 psi), but other pressure differentials are also contemplated. The frangible seal 128 may be attached to the mouth 104 via heat-sealing (as in, for example, direct heat, induction heat or vibration generated heating processes), by gluing or using another adhesive, and/or by any other suitable method.

The drainage system 100 may be packaged and shipped as an assembly that includes the container 102 with the interior 112 sealed by the frangible seal 128. When packaged and shipped (or otherwise transported), the interior 112 of the container 102 is preferably pre-loaded with a vacuum (and herein, a "vacuum" may refer to an environment with relatively low pressure with respect to an external environment, but "vacuum" does not necessarily require the space to be entirely devoid of matter). It is also contemplated that the vacuum may be loaded by the patient (e.g., by hooking the container 102 to a vacuum pump).

To perform a drainage procedure, the distal end (not shown) of the drainage line 116 may be attached to a collection device that is at least partially placed into a target space in the body of a patient. For example, the collection device (not shown) may include a catheter that can be placed in the pleural space of the patient to remove excess pleural fluid via a needle within the body of the patient. Once the drainage line 116 is appropriately coupled to the collection device, the spike 122 may be pushed towards the container 102 by applying a downward (distal-facing) force to the flange 132. This force may deform the cap 114, and particularly the widened body 120 of the cap 114 in the depicted embodiment, such that the spike 122 moves distally and such that the point 134 of the spike 122 pierces the frangible seal 128. When the frangible seal 128 is pierced, the vacuum loaded within the interior 112 of the container 102 may communicate with the drainage line 116 to draw fluid (including gasses and liquids) from the target space of the patient body and/or the collection device, through the drainage line 116, and ultimately into the interior 112 of the container 102.

It may be important to be able to verify at a glance that the vacuum in the interior 112 of the container 102 is intact to ensure suitable operation. In some embodiments, this can be accomplished through recognition of deformation of the cap 114 (which, as stated above, may be formed of an elastomeric material). In its default position (i.e., when not exposed to the vacuum), the cap 114 may appear substantially different than it may appear when exposed to the vacuum of the interior 112. For example, when exposed to the vacuum, the widened body 120 of the cap 114 may at least partially collapse. This partial collapse will thus be apparent to the user and will verify the existence of the vacuum. The state of the cap 114 may further indicate the state of the vacuum as the drainage procedure continues, and the cap 114 may indicate that the vacuum has been exhausted when it returns fully to its default state.

Optionally, the cap 114 may be secured to the container 102 via a silicone adhesive, and/or an O-ring may be located between the cap 114 and the underlying mouth 104 of the container 102 to ensure a suitable seal. Embodiments utilizing an adhesive and embodiments with an O-ring are described in detail in U.S. patent application Ser. No. 14/788,198, filed Jun. 30, 2015, and published Jan. 5, 2017, which is incorporated by reference herein in its entirety. Additionally or alternatively, retention ring 140 (which may also be referred to as a retaining ring) may be included to facilitate securement of the cap 114 to the container 102. The retention ring 140 may be formed integrally (e.g., by injection molding, 3D printing, or another suitable method), and may be formed of any suitable material. In certain non-limiting exemplary embodiments, the retention ring 140 may be formed of a polypropylene material or a nylon.

Figure 2:
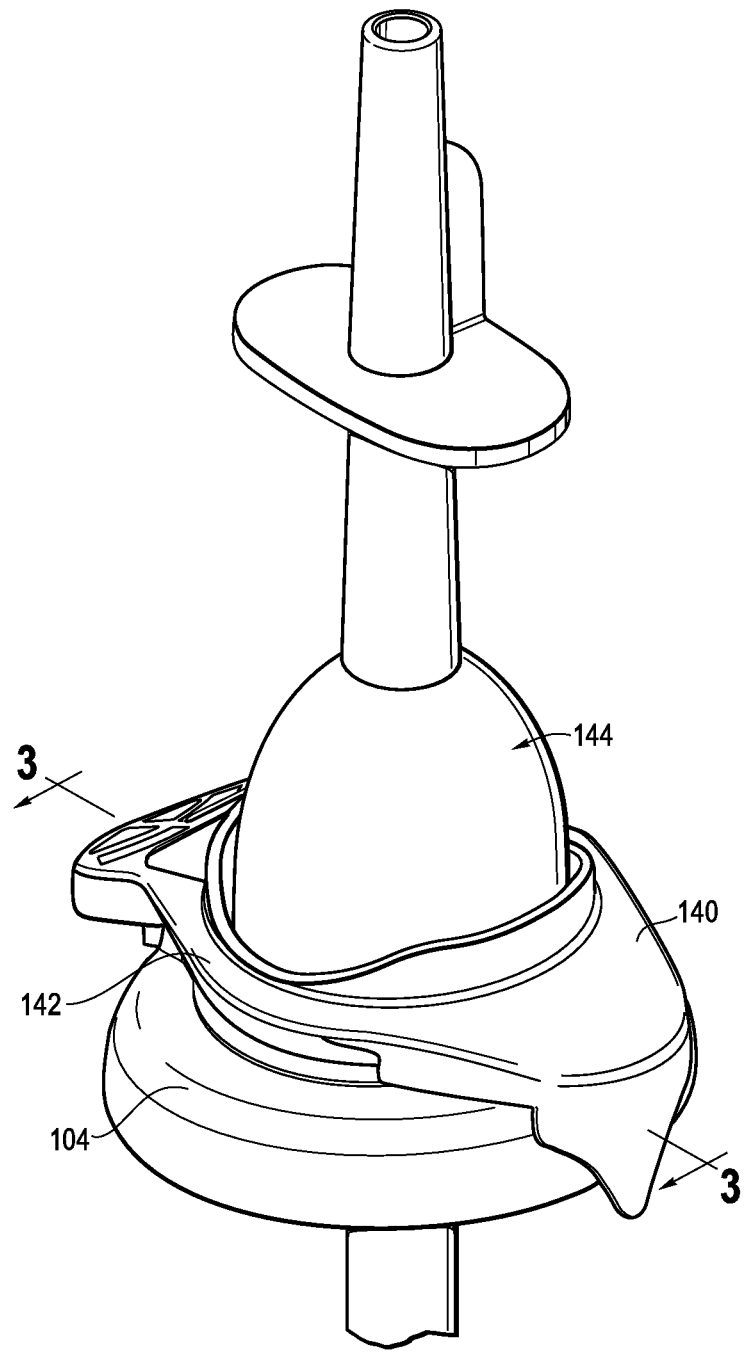
FIG. 2 is an illustration showing a side perspective view of a portion of the drainage system with a retention ring.

FIG. 2 is an illustration showing a side perspective view of a portion of the drainage system 100. As shown, the retention ring 140 may have a collar 142 that circumferentially engages an outer surface 144 of the cap 114, thereby squeezing or otherwise providing a constricting force to retain the cap 114 in engagement with the mouth 104 of the container 102. This constriction provided by the retention ring 140 may compress the elastomeric material of the cap 114 against the mouth 104 of the container 102, thus providing a seal. The retention ring 140 may be installed (i.e., manipulated into its position around the cap 114 and mouth 104 as shown in FIG. 2) by a user prior to a drainage procedure when attaching the cap 114 to the container 102, or the retention ring 140 may be installed prior to packaging and shipping of the drainage system 100.

Figure 3:
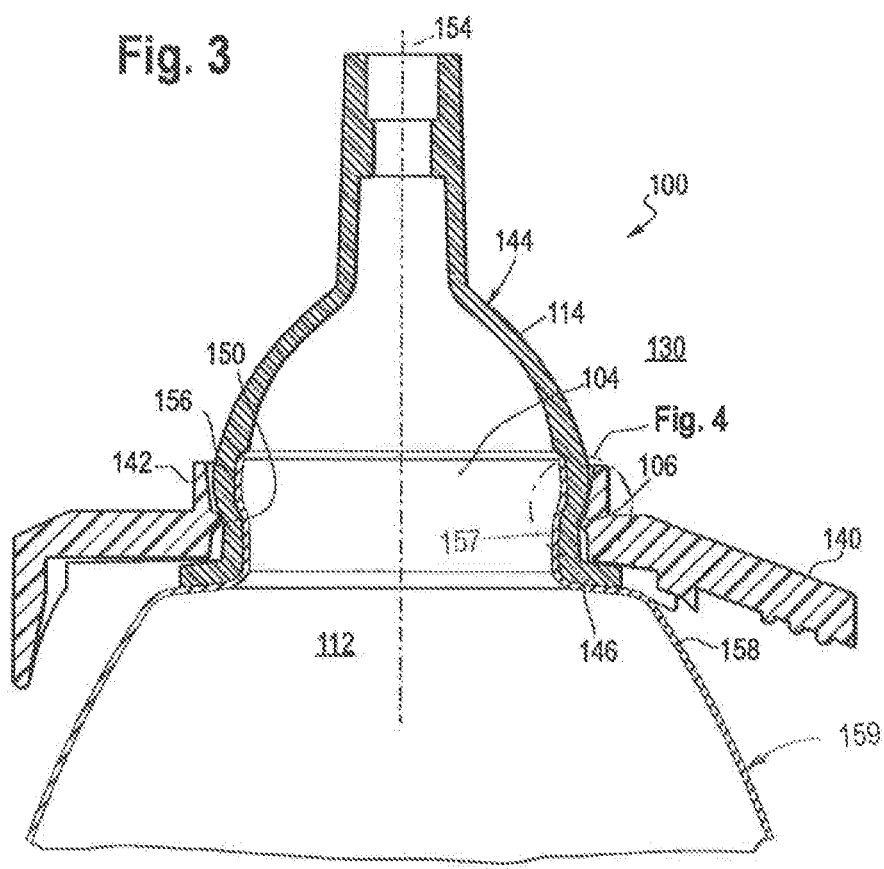
FIG. 3 is an illustration showing a side section view of a portion of the drainage system of FIG. 2 about line 3-3.
Figure 4:
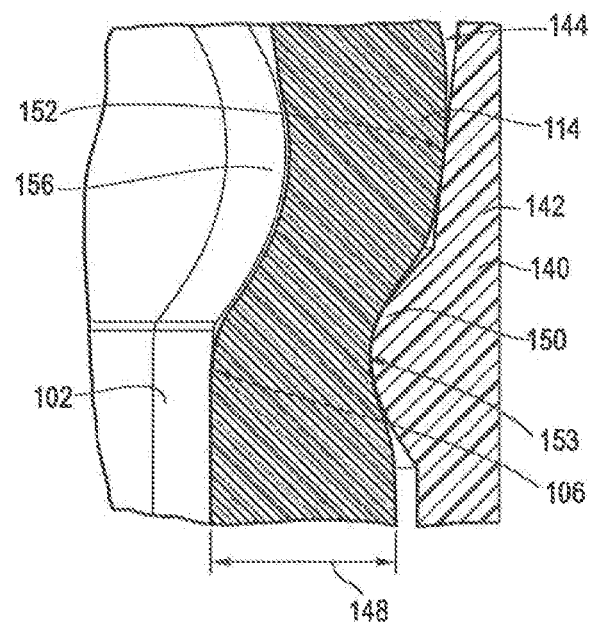
FIG. 4 is an illustration showing a magnified view of a portion of FIG. 3.

FIG. 3 shows a side section view of a portion of the drainage system 100 of FIG. 2 about line 3-3, and FIG. 4 shows a magnified view of a portion of FIG. 3. As shown in FIGS. 3-4, and as described above, the collar 142 of the retention ring 140 may circumferentially engage the cap 114. The collar 142 of the retention ring 140 may be sized such that it provides a constriction force on the outer surface 144 of the cap 114 when the cap 114 is located over the mouth 104 of the container 102. For example, the retention ring 140 may include the collar 142 with an inner diameter that is slightly larger than an outer diameter defined by the outer surface 106 of the mouth 104. The cap 114 may have a default thickness 148 (e.g., a thickness when not deformed by the retention ring 140). In one non-limiting exemplary embodiment, the default thickness may be about 0.075 inches in at least some locations, but other suitable dimensions are also contemplated (e.g., the default thickness may be between about 0.010 inches and about 0.150 inches, such as between about 0.060 inches and about 0.080 inches). Adjacent to where the retention ring 140 engages the cap 114 during a drainage procedure, the cap 114 may be compressed such that the thickness at the area where the retention ring 140 engages the cap 114 is smaller than the cap's default thickness. The compression between the outer surface 106 of the mouth 104 and the collar 142 of the retention ring 140 may create or enhance a seal between the cap 114 and the mouth 104. This seal may retain the above-described pressure differential between the interior 112 of the container 102 and the external environment 130 and also may prevent leakage of fluid during drainage.

As depicted in FIG. 4, the retention ring 140 may include a bead 150 located on an inner surface 152 of the collar 142 of the retention ring 140, where the inner surface 152 defines the inner diameter of the collar 142. While only one bead 150 is shown in the present figure, more than one bead may be included. The bead 150 may have an apex 153, which may be closer to an axis 154 through the center of the collar 142 of the retention ring 140 relative to adjacent areas of the inner surface 152. While any suitable dimensions are contemplated, the bead 150 may be an arc with a diameter of about 0.052 inches, and the apex 153 may be about 0.575 inches from the center of the collar 142 at its closest point. The apex 153 of the bead 150 may be formed integrally with the remainder of the retention ring 140 (e.g., through a common injection molding process, 3D printing process, or other suitable process), or it may be installed after formation of the remainder of the retention ring 140. The apex 153 may be advantageous for concentrating the above-described constriction force on a relatively small area of the cap 114 when the retention ring 140 is engaged with the cap 114 around the mouth 104 of the container 102, as shown in FIG. 4. The resulting deformation of the relatively small area receiving a high proportion of the constricting force may provide an enhanced seal between the mouth 104 and the cap 114 with respect to other embodiments. In exemplary embodiments, the constriction force may provide at least 50 psi of contact pressure between the cap 114 and the mouth 104 adjacent to the apex 153 around the entirety of the mouth 104, and the contact pressure may be significantly higher in certain locations. Further, the concentration of the contraction force may provide enhanced ability to retain the seal between the mouth 104 and the cap 114 over relatively long period of time (e.g., 2 years or more), which is advantageous for supply-chain efficiency due to the ability to store the system for a relatively long time period prior to use.

Optionally, as shown FIG. 4, the mouth 104 of the container 102 may include a protrusion 156 around the outer diameter defined by the outer surface 106 of the mouth 104. The protrusion 156 may have dimensions similar to the bead 150 with respect to the outer surface 106 of the mouth 104, but this is not required. The protrusion 156 may be located just proximal (above) the bead 150 of the retention ring 140 when the retention ring 140 is installed, but other locations are also contemplated. Like the bead 150, the protrusion 156 may be advantageous for concentrating compression at a relatively small area of the cap 114 to provide an enhanced seal. Additionally or alternatively, the protrusion 156 may retain the retention ring 140 in place by preventing distal-to-proximal movement of the retention ring 140 relative to the mouth 104 when the retention ring 140 is installed around the cap 114 and mouth 104. In some embodiments, the cap 114 may also (or alternatively) include a protrusion 156 and/or a channel for receiving the bead 150 to facilitate suitable positioning of the retention ring 140 with respect to the cap 114.

The protrusion 156 and/or the bead 150 may be rounded or otherwise shaped such that, when a force is applied to the retention ring 140 to install the retention ring 140 around the mouth 104 or remove the retention ring 140, at least one of the mouth 104 and the retention ring 140 slightly deforms to allow passage of the bead 150 beyond the protrusion. In exemplary embodiments, the retention ring 140 may be more easily deformed than the mouth 104. As shown in FIG. 3, the protrusion 156 and/or the bead 150 may be positioned on their respective elements such that, when installed, the retention ring 140 is forced into a position such that it extends downward alongside a neck 157 and contacts a shoulder 158 of a main body 159 of greatest volume located below the neck 157 of the container 102 and/or a lip 146 of the cap 114 thereby pinning the lip 146 between the retention ring 140 and the shoulder 158 of the main body 159 as shown by FIG. 4. As a result, the retention ring 140 may be substantially fixed in place with respect to the mouth 104 and cap 114 when installed (absent a removal force).

Figure 5:
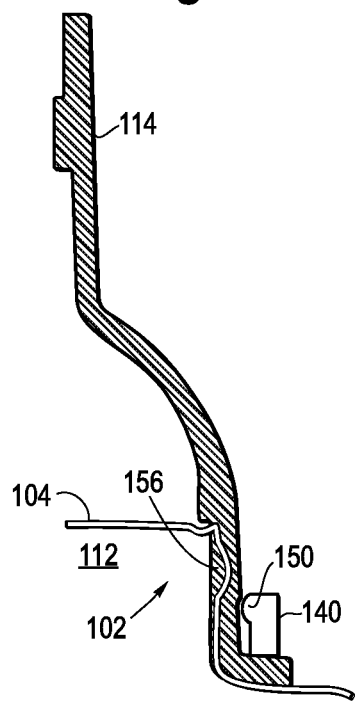
FIG. 5 is an illustration showing a side view of a portion of the drainage system to illustrate the relative non-deformed state of certain components.
Figure 6:
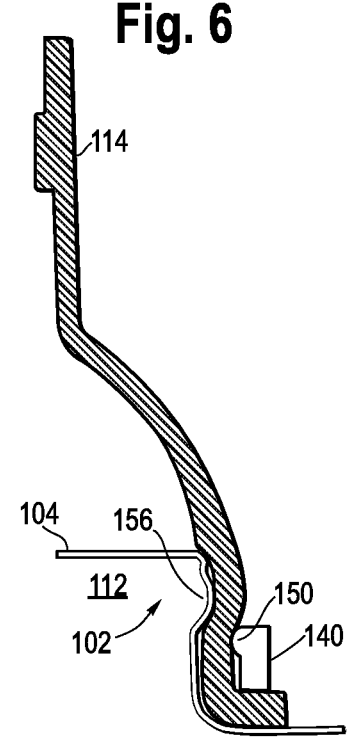
FIG. 6 is an illustration similar to FIG. 5, but showing the components as they may appear as deformed when the retention ring is installed.
Figure 7:
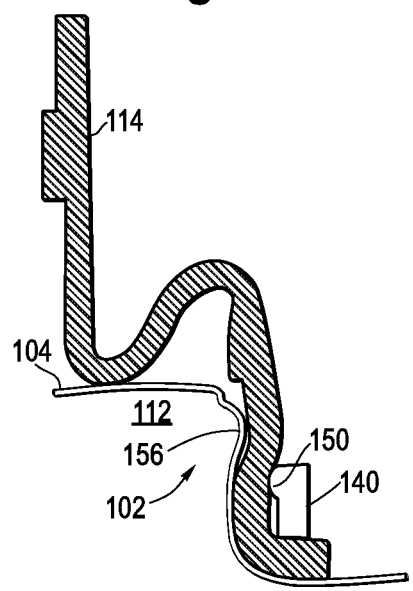
FIG. 7 is an illustration similar to FIG. 6, but showing the components as they may appear as deformed when the retention ring is installed and the interior of a cap of the drainage system is exposed to a vacuum.

FIGS. 5-7 are figures showing a portion of the drainage system 100 to further illustrate the respective fits of the cap 114 around the mouth 104 and the retention ring 140 around the cap 114. FIG. 5 shows the cap 114 as it may appear relative to the mouth 104 and the retention ring 140 when the cap 114 is not deformed. As shown, the protrusion 156 and the bead 150 may extend into the default path of the cap 114. As a result of this feature, the cap 114 may be forced to deform when the cap 114 is installed around the mouth 104 and/or the retention ring 140 is installed around the cap 114 as shown in FIG. 6. A bead gap, which may be defined as the shortest distance between the protrusion 156 and the bead 150 in the horizontal direction of FIG. 6, may be approximately 0.036 inches. As described above (with reference to FIG. 4), the dimensions and orientation of the protrusion 156, the bead 150, and the remainders of the mouth 104 and retention ring 140 may cause the material of the cap 114 to compress, thereby enhancing the seal. In other words, the above-described bead gap may be smaller than the default thickness of the cap 114 (see FIG. 4). In some embodiments, the cap 114 may compress to about 20% to about 80% of its default thickness (e.g., about 50%) when the retention ring 140 is engaged. FIG. 7 is similar to FIG. 5, but shows the above-described elements as they may appear when the interior of the cap 114 is exposed to the vacuum provided by the interior 112 of the container 102. The cap 114 may be formed of a material that is relatively compliant or otherwise compressible. In some non-limiting examples, the cap 114 may be substantially formed by Mediprene™ 500700M-02 supplied by HEXPOL TPE or Santoprene™ 8281-65MED supplied by ExxonMobile.

Figure 8:
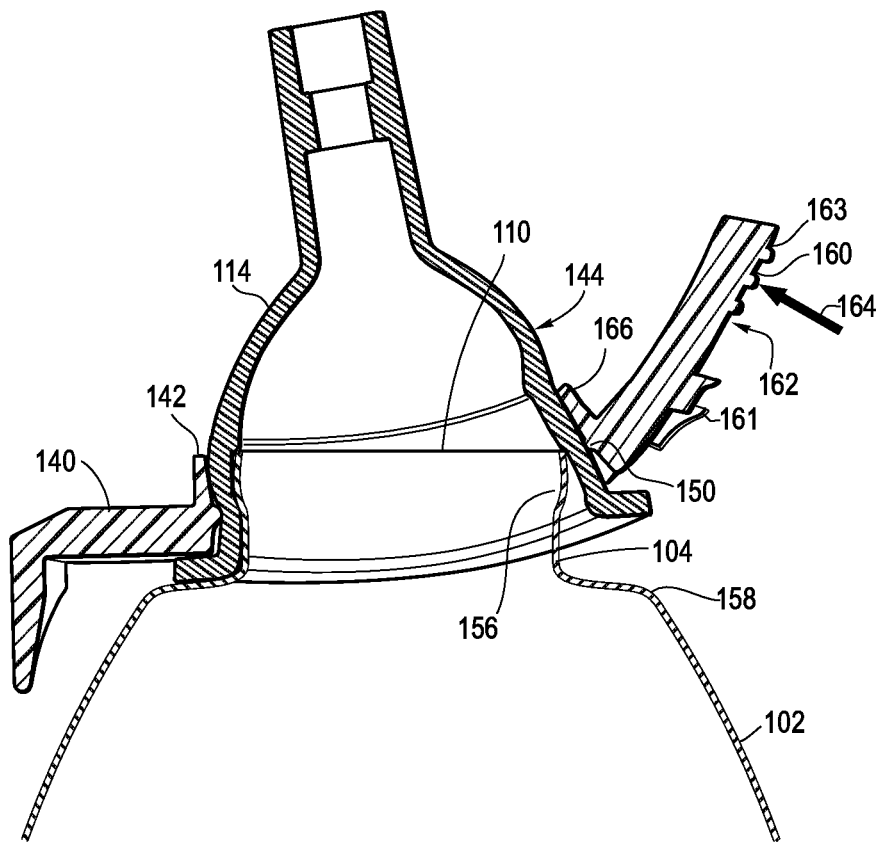
FIG. 8 is an illustration showing a side section view of the retention ring depicted in FIG. 2 about line 3-3, where the retention ring is deformed due to a force provided on a tab of the retention ring.

FIG. 8 is an illustration showing a side section view of the retention ring 140, where the retention ring is deformed due to a force provided on a tab 160 of the retention ring 140. The tab 160 may be integrally formed (e.g., injection molded) with the remainder of the retention ring 140. The tab 160 may include a surface 162 facing approximately distally, where the surface 162 is configured to receive a removal force provided by a user (e.g., through contact and pressure with a finger on the surface 162, for example). As shown, the surface 162 may optionally include grip elements 163 for suitable friction/grip with a finger or hand of a user. Optionally, the tab 160 may include an extension 161 that is configured to abut the shoulder 158 of the container 102 when the retention ring 140 is installed. In some embodiments, the shoulder 158 may be spaced from the extension 161 unless a downward force is provided on the tab 160, thus engaging the extension 161 with the shoulder 158. Advantageously, when a downward force is provided (e.g., inadvertently), the extension 161 may transfer the force to the shoulder 158 to prevent the retention ring 140 from deforming to a degree such that it is inadvertently removed from its engaged state.

As depicted, when a sufficient force (such as the depicted removal force 164) is provided, the retention ring 140 may deform. As described in more detail below (with reference to FIG. 8), a rim portion of the retention ring 140 may be more easily deformed than other portions of the retention ring 140 such that the retention ring 140 deforms in a particular manner such that it manipulates itself out of engagement with the mouth 104 when the removal force 164 is provided. Optionally, the retention ring 140 may include a lip 166 on the proximal side of the collar 142. In some embodiments, the lip 166 may taper outwards such that it is not snug with the mouth 104. In other embodiments, the lip 166 may be flush with the mouth 104. Additionally or alternatively, the lip 166 may be configured to engage with a proximal end 110 of the mouth 104 (e.g., through the thickness of the cap 114) when the removal force 164 is applied such that the lip 166 pivot around the mouth 104 and presses into the cap 114. The partial collapse of the cap 114 due to this pressure may enhance the ability of the retention ring 140 to remove the cap 114 and/or may reduce the minimum remove force 164 sufficient for cap removal. The pivot of the lip 166 may additionally or alternatively cause the lip 166 to press distally against the proximal end 110 of the mouth 104 (e.g., through the compliant material of the cap 114), thereby facilitating proximal removal of the retention ring 140 from the mouth 104. In other words, a lever-like effect of the lip 166 pressing against the mouth 104 and/or the outer surface 144 of the cap 114 may assist in deforming the retention ring 140 such that the bead 150 can pass the protrusion 156 of the mouth 104 of the container 102. In some exemplary embodiments, a removal force of between about 2 pounds and 16 pounds may be sufficient to remove the retention ring 140, such as about 7.8 pounds at nominal conditions. This force required for removal may vary depending on the specific dimensions of the cap 114, retention ring 140, and mouth 104, as well as the materials forming these elements and the friction coefficient between said elements. The retention ring 140 may be designed such that different removal forces are adequate in other embodiments, and it is contemplated that the minimum force for removing the retention ring 140 may change as the drainage system ages.

Only one tab 160 is depicted in FIG. 8, but more than one tab 160 may be included. For example, it may be advantageous to provide a tab 160 on opposite sides of the collar 142 of the retention ring 140 such that a user can provide removal forces on the respective opposite sides of the collar 142. It is further contemplated that the tab 160 may include a surface on its proximal side and related elements (e.g., elements to provide a lever-like effect) configured to receive an installation force by a user or other person when installing the retention ring 140 around the mouth 104 and/or cap 114.

Figure 9:
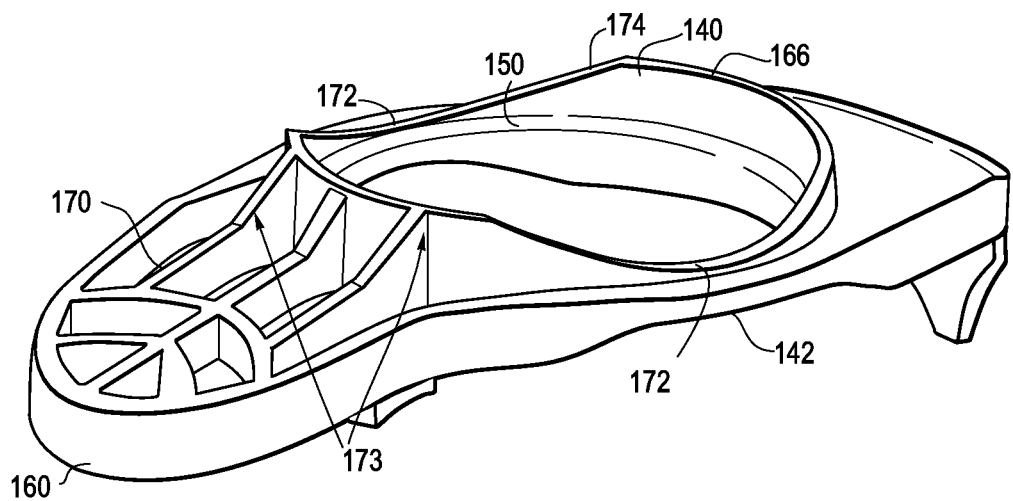
FIG. 9 is an illustration showing a perspective view of a tab of the retention ring of the drainage system.

Referring to FIG. 9, which is an illustration showing a perspective view of the retention ring 140, the proximal side of the tab 160 may optionally include structural ribs 170 and/or other structural features such that the tab 160 is relatively stiff (at least when compared to portions of the collar 142). The ribs 170 may in particular provide stiffness to the tab 160 such that when the tab 160 receives a force, the force is primarily transferred through the ribs 170 to the collar 142 of the retention ring 140 without substantially deforming the tab 160 and thus enhancing the ability of the retention ring 140 to focus the deformation of the retention ring 140 at a certain location of the collar 142. The ribs 170 may include gussets 173 extending to the lip 166 of the collar 142 to further transfer the force in a desired manner and to increase the force required to initiate undesirable buckling of the tab 160. In certain non-limiting exemplary embodiments, the ribs 170 may be approximately 0.050 inches in thickness, which may be an optimal thickness for providing adequate strength without unduly increasing component cost or decreasing manufacturing efficiency.

Figure 10:
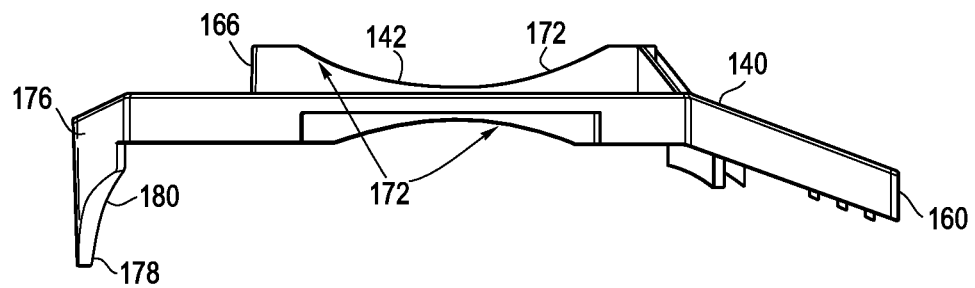
FIG. 10 is an illustration showing a side view of the retention ring of the drainage system.

FIG. 10 is an illustration showing a side view of the retention ring 140. As shown in FIGS. 9-10, the collar 142 of the retention ring 140 may include one or more bendable collar portions 172 that are relatively deformable with respect to other portions of the retention ring 140, such as the remainder of the collar 142, the tab 160, etc. The bendable collar portions 172 may have relatively small cross-sectional dimensions with respect to the remainder of the collar 142 such that, when subjected to a force, the collar 142 tends to deform primarily at the bendable collar portions 172. While any suitable dimensions are contemplated, in some embodiments, the bendable collar portions 172 may include a cutout 174 located at least in the lip 166 and that is shaped as an arc with a radius of approximately 1 inch. If the cutout 174 is in the shape of an arc, the edges of the bead 150 (shown in FIG. 9) may optionally be approximately tangent to the arc of the cutout 174. These dimensions may be optimal for certain applications by maximizing the flexibility of the collar 142 at the bendable collar portions 172 without interrupting the function(s) of the bead 150. The cutout 174 may reduce the bending moment of inertia during removal of the collar 142 to thereby reduce the load required to remove the retention ring 140.

Figure 11:
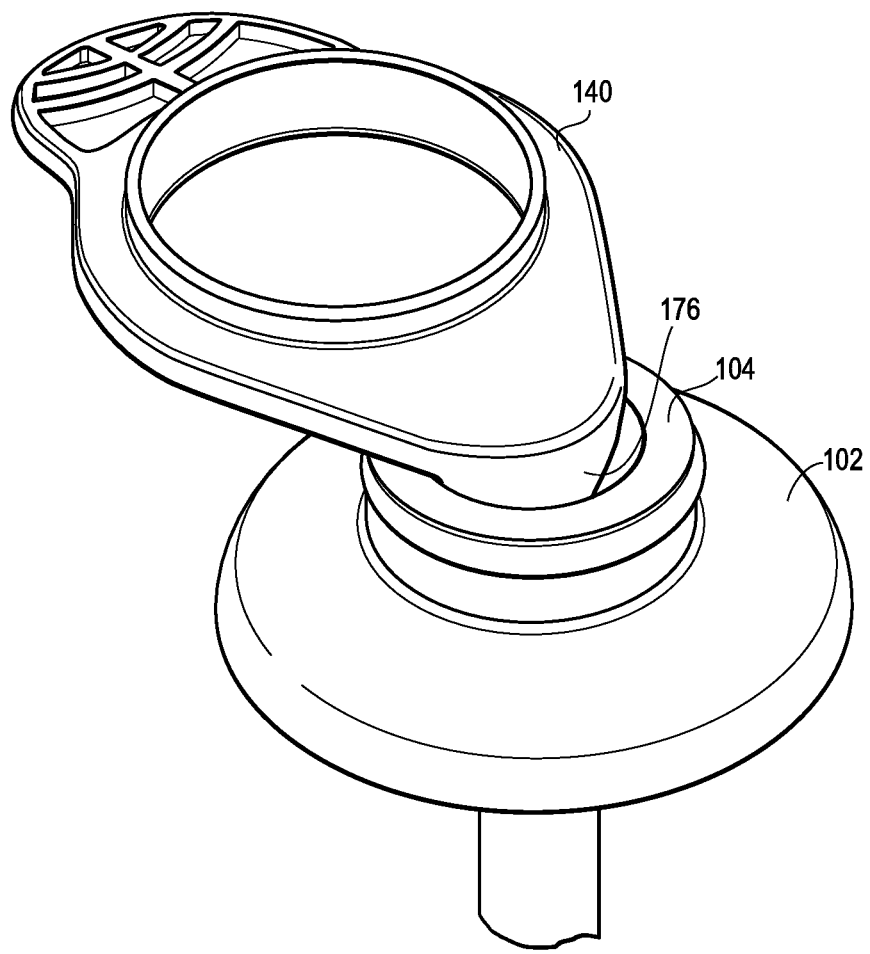
FIG. 11 is an illustration showing another side perspective view of the retention ring as a prong of the retention ring opens a frangible seal coupled to a mouth of a container.

Referring to FIG. 10, the retention ring 140 may include a prong 176. The prong 176 may be configured to open the frangible seal 128 by piercing the frangible seal 128 (see FIG. 1) with a spike or point 178. As described above, the frangible seal 128 may initially be pierced by a spike 122 (shown in FIG. 1) during a drainage procedure. However, when it is desirable to drain the container 102 after the drainage procedure, the piercing of the frangible seal 128 may not have a sufficient opening for efficient removal of fluid or solid medical waste from the container 102 after a drainage procedure. Further, in embodiments where it is advantageous to add a solidifier to fluid waste within the container 102 prior to disposal, a relatively large opening (e.g., larger than used during drainage) may be advantageous for simplifying the deployment of the solidifier without the use of a funnel, for example. Thus, the present embodiments may be advantageous because after the drainage procedure, a user (e.g., a patient) may remove the retention ring 140 from the mouth 104 (as described above) and then use the prong 176 of the retention ring 140 to further open the frangible seal 128 such that its opening is sufficient for drainage. Thus, at least the point 178 of the prong 176 may be sized, shaped, and/or otherwise configured to increase the size of the opening in the frangible seal 128 through manipulation of an edge 180 of the prong 176 through the frangible seal 128 by a user. The prong 176 may be relatively rigid when compared to the frangible seal 128. FIG. 11 shows the prong 176 when used to increase the opening of a frangible seal at the mouth 104 of the container 102.

Figure 12A:
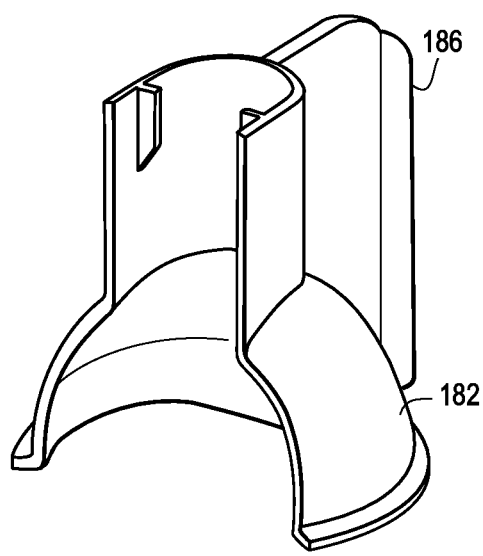
FIGS. 12A-D are illustrations showing a side perspective view of the drainage system incorporating a safety clip.
Figure 12B:
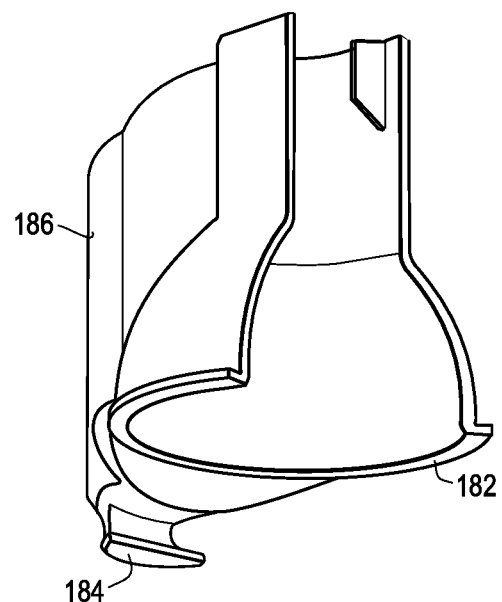
Figure 12C:
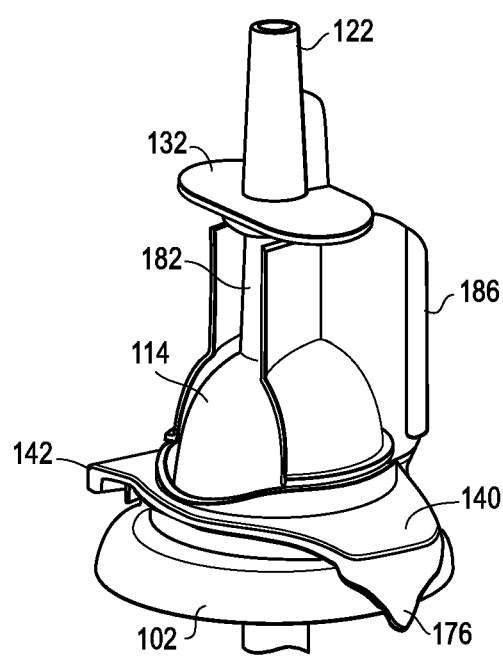
Figure 12D:
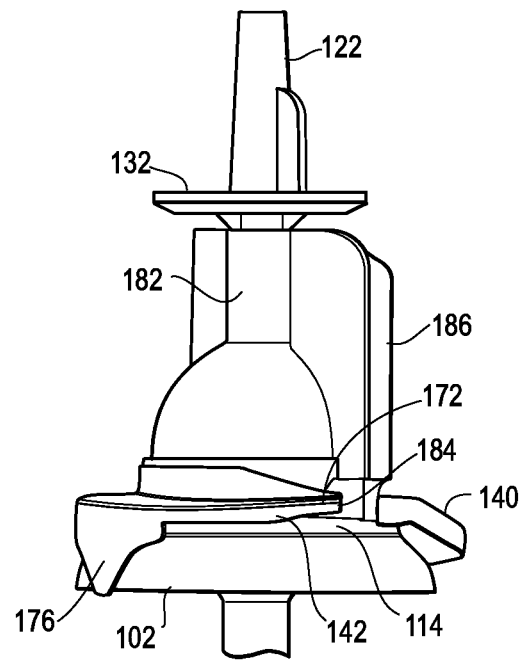

As shown in FIGS. 12A-D, the drainage system 100 may include a safety clip 182 that fits around the cap 114. When the drainage system 100 is initially assembled, the safety clip 182 engaged with the cap 114 such that it is located around the cap 114 and between the flange 132 of the spike 122 and the container 102. The safety clip 182, when engaged, may prevent the spike 122 from moving distally and puncturing the frangible seal 128 prematurely. As shown in FIG. 12D, the safety clip 182 may include a groove 184 that is configured (e.g., sized and shaped) to fit around at least a portion of the collar 142 of the retention ring 140. The engagement between the groove 184 and the retention ring 140 may retain the safety clip 182 in place by preventing its motion in the distal and/or proximal direction. Further, when groove 184 is sized and shaped to fit around at least one of the relatively narrow rim portions 172 (which may incorporate a curve, as described above), the size of the groove 184 with respect to the curve of the rim portions 172 may prevent rotation of the safety clip 182. The safety clip 182 may be removed by a user by pulling on a handle 186, and the drainage procedure may be initiated through movement of the spike 122 when the safety clip 182 is removed (e.g., to pierce a frangible seal as described above). While not shown, it is contemplated that the safety clip 182 may have a prong similar or identical to the prong 176 of the retention ring 140 (e.g., as an alternative to including the prong 176 of the retention ring 140). In some embodiments, the extension holding the groove 184 (or another extension) may be configured (sized and shaped) such that it can be used to engage the retention ring 140 when the retention ring 140 is being removed, thereby providing a user with a tool to assist in removal of the retention ring 140 from its engaged state. Additionally or alternatively, the safety clip 182 may include a visual indicator (e.g., a molded arrow) depicting the direction that a user must pull to remove the safety clip 182 from the cap 114, thus providing instructions to a user for initiation of a drainage procedure.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A drainage system, the drainage system comprising:
   a container having an interior and a mouth, the mouth having an outer surface and an opening;
   a frangible seal covering the opening;
   a cap secured to the mouth and in fluid communication with a drainage line, the cap having an inner surface for engaging the outer surface of the mouth; and
   a retention ring having a distally facing surface and comprising a collar having an inner surface configured to engage an outer surface of the cap, the collar terminating at a proximal edge of the retention ring,
   wherein the retention ring includes a bead spaced from both the distally facing surface and the proximal edge, the bead having an increased cross-sectional thickness compared to the collar such that the bead extends toward the cap to an apex for at least partially concentrating a restriction force provided by the retention ring on an adjacent area of the outer surface of the cap, the restriction force concentrated by the bead compressing a thickness of the cap at the bead to less than a default thickness;
   wherein a lip of the cap extends along a shoulder of a main body of the container between the retention ring and the shoulder, the retention ring extending outward beyond the bead to pin the lip between the retention ring and the shoulder.

2. The drainage system of claim 1, wherein the outer surface of the mouth includes a protrusion, and wherein the bead of the retention ring is located distally of the protrusion of the mouth.

3. The drainage system of claim 1, wherein the retention ring includes a tab extending from the collar, the tab having a surface for receiving a removal force.

4. The drainage system of claim 3, wherein the collar of the retention ring includes a collar portion having a relatively low bending moment of inertia with respect to adjacent areas of the collar such that the collar portion deforms in response to the removal force being received by the tab.

5. The drainage system of claim 3, wherein the surface of the tab of the retention ring faces distally, and wherein the tab of the retention ring includes a rib on its proximal side extending to a lip of the collar.

6. The drainage system of claim 1, wherein the retention ring includes a prong with a point for increasing the size of an opening of the frangible seal.

7. The drainage system of claim 1, further comprising:
   a spike with a flange, the spike being configured to pierce the frangible seal in response to an initiation force being applied to the flange in a distal direction; and
   a safety clip engaged with the cap and located at least partially between the flange of the spike and the retention ring.

8. The drainage system of claim 7, wherein the safety clip includes a groove for receiving at least a portion of the collar of the retention ring.

9. A cap assembly for a drainage system, the cap assembly comprising:
   a cap configured to be secured to a mouth of a container and having an opening for communication with a drainage line, the cap having an inner surface that engages an outer surface of the mouth;
   a retention ring having a distally facing surface and comprising:
      a collar having an inner surface forming a generally circular opening, the collar terminating at a proximal edge of the retention ring, the collar terminating at a proximal lip of the retention ring at or distal of a terminal edge of the mouth; and
      a bead spaced from both the distally facing surface and the proximal edge, the bead extending from the inner surface of the collar, the bead having an increased cross-sectional thickness compared to the collar such that the bead extends toward the cap to an apex for at least partially concentrating a restriction force on an adjacent area of an outer surface of the cap, the restriction force concentrated by the bead compresses a thickness of the cap at the bead to less than a default thickness with the cap and retention ring secured to the mouth of the container;
      wherein the retention ring extends outward beyond the bead to pin the lip between the retention ring and a shoulder of a main body of the container.

10. The cap assembly of claim 9, further comprising a tab extending from the collar, the tab having a surface for receiving a removal force.

11. The cap assembly of claim 10, wherein the collar of the retention ring includes a collar portion having a relatively low bending moment of inertia with respect to adjacent areas of the collar such that the collar portion deforms in response to the removal force being received by the tab.

12. The cap assembly of claim 10, wherein the surface of the tab of the retention ring faces distally, and wherein the tab of the retention ring includes a rib on its proximal side extending to the proximal lip of the collar.

13. The cap assembly of claim 12, wherein the rib includes a gusset extending to the proximal lip.

14. The cap assembly of claim 9, wherein the retention ring includes a prong with a point for increasing the size of an opening of a frangible seal.

15. The cap assembly of claim 9, wherein the retention ring is substantially formed through a 3-D printing process.

16. The cap assembly of claim 9, wherein the retention ring includes at least one of a polypropylene material and a nylon material.

17. A method comprising:
piercing a frangible seal with a spike, wherein the frangible seal covers an opening of a mouth of a container; and
exposing a drainage line to a vacuum initially contained in an interior of the container,
wherein a cap provides fluid communication between the interior of the container and the drainage line,
wherein the cap is engaged with an outer surface of the mouth,
wherein a seal is provided between the outer surface of the mouth and the cap by a compression force,
wherein the compression force is provided by a collar of a retention ring, the collar including an inner surface positioned in engagement with an outer surface of the cap, and
wherein the inner surface of the collar includes a bead for at least partially concentrating the compression force on an area of the cap adjacent to the bead, the bead spaced from both a distally facing surface of the retention ring and a proximal edge of the collar, the bead having an increased cross-sectional thickness compared to the collar such that the bead extends toward the cap to an apex, the restriction force concentrated by the bead compressing a thickness of the cap at the bead to less than a default thickness;
wherein a lip of the cap extends along a shoulder of a main body of the container between the retention ring and the shoulder, the retention ring extending outward beyond the bead to pin the lip between the retention ring and the shoulder.

18. The method of claim 17, wherein the outer surface of the mouth includes a protrusion, and wherein the bead of the retention ring is located distally of the protrusion of the mouth.

19. The method of claim 17, further comprising:
removing the retention ring from engagement with the cap by applying a removal force to a tab of the retention ring, wherein the tab of the retention ring is coupled to the collar of the retention ring, and wherein a collar portion of the collar bends in response to the application of the removal force.

20. The method of claim 17, further comprising increasing the size of an opening of the pierced frangible seal by manipulating a prong of the retention ring through the opening.

* * * * *